United States Patent [19]

Vassiliadis et al.

[11] Patent Number: 5,129,895
[45] Date of Patent: Jul. 14, 1992

[54] LASER SCLEROSTOMY PROCEDURE

[75] Inventors: Arthur Vassiliadis, Mountain View; David R. Hennings, Newcastle, both of Calif.

[73] Assignee: Sunrise Technologies, Inc., Sunnyvale, Calif.

[21] Appl. No.: 525,165

[22] Filed: May 16, 1990

[51] Int. Cl.⁵ ............................................. A61N 5/06
[52] U.S. Cl. .................................... 606/6; 606/3; 606/15; 606/17
[58] Field of Search ............... 128/385, 397, 398, 897, 128/898; 606/2–4, 6, 7, 13–18

[56] References Cited

U.S. PATENT DOCUMENTS

| | | | |
|---|---|---|---|
| 3,843,391 | 9/1974 | Block | 606/16 |
| 4,740,047 | 4/1988 | Abe et al. | 606/7 |
| 4,799,479 | 1/1989 | Spears | 606/7 |
| 4,860,743 | 8/1989 | Abela | 606/7 |

FOREIGN PATENT DOCUMENTS

| | | | |
|---|---|---|---|
| 0163266A2 | 12/1985 | European Pat. Off. | |
| 214712 | 3/1987 | European Pat. Off. | 606/3 |

*Primary Examiner*—David M. Shay
*Attorney, Agent, or Firm*—Majestic, Parsons, Siebert & Hsue

[57] ABSTRACT

A fiber optic probe and its use in performing a sclerostomy (forming a small hole in the sclera of an eye) as a treatment of glaucoma. The minimally dimensioned probe is designed to direct laser light out of its side and, as a result, allows a sclerostomy procedure to be performed with minimal trauma to the conjunctiva and other surrounding ocular tissues of the patient. A series of pulses of infrared laser radiation delivered through the side of the probe forms the hole in the sclera.

7 Claims, 3 Drawing Sheets

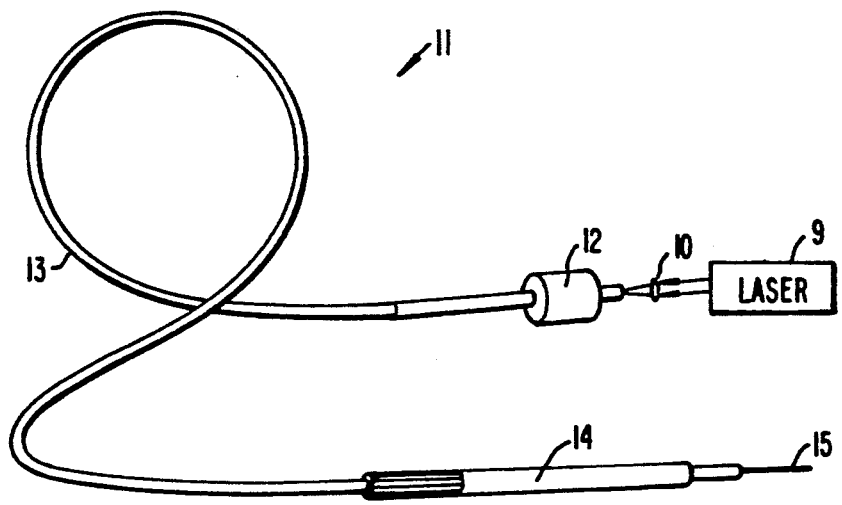
FIG._1.
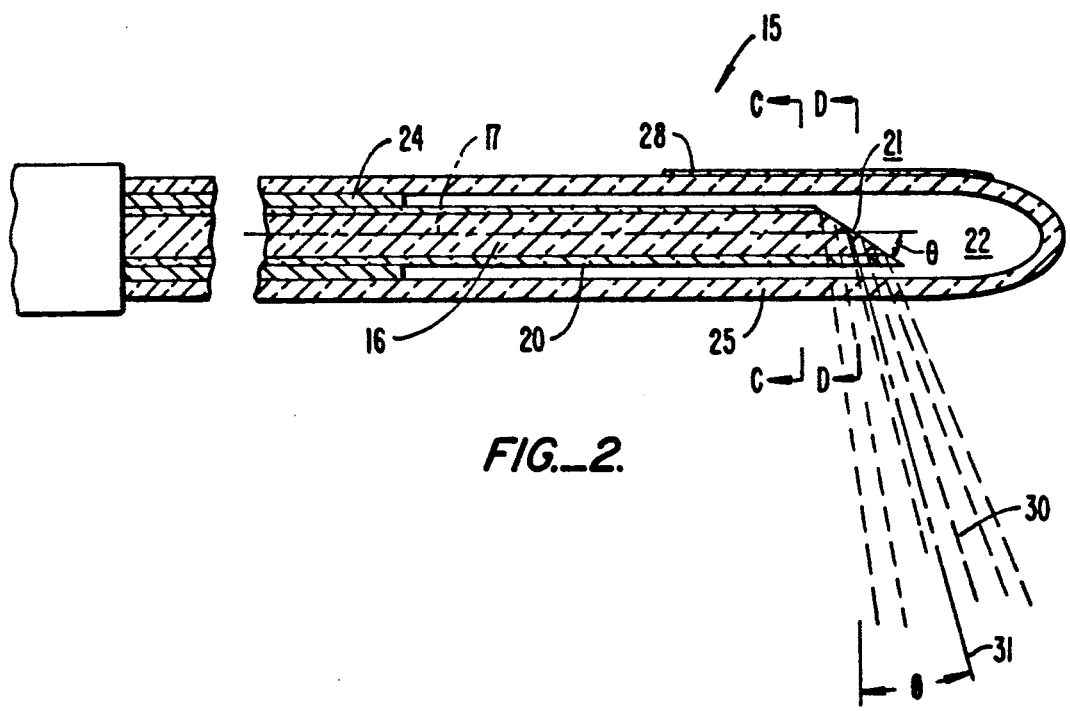
FIG._2.
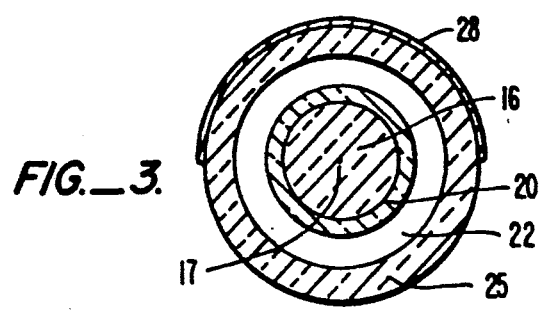
FIG._3.

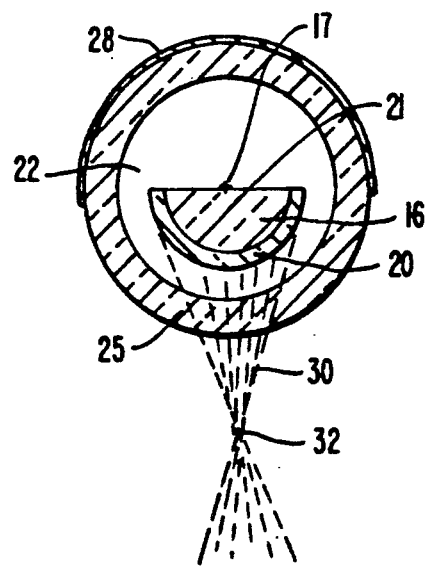
FIG._4.
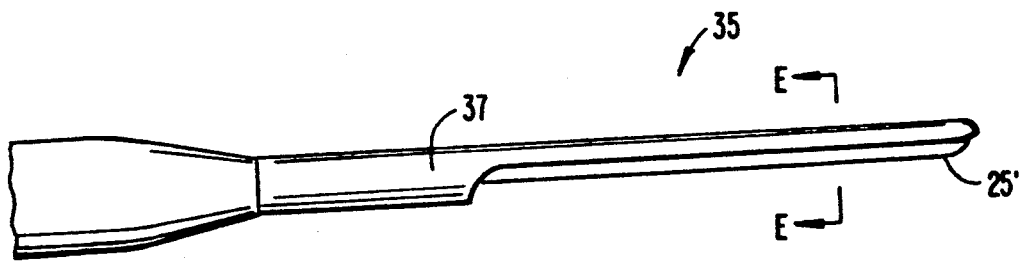
FIG._5.
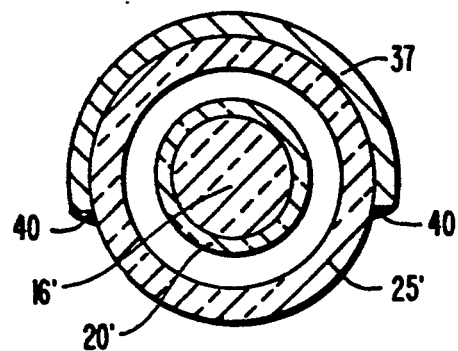
FIG._6.

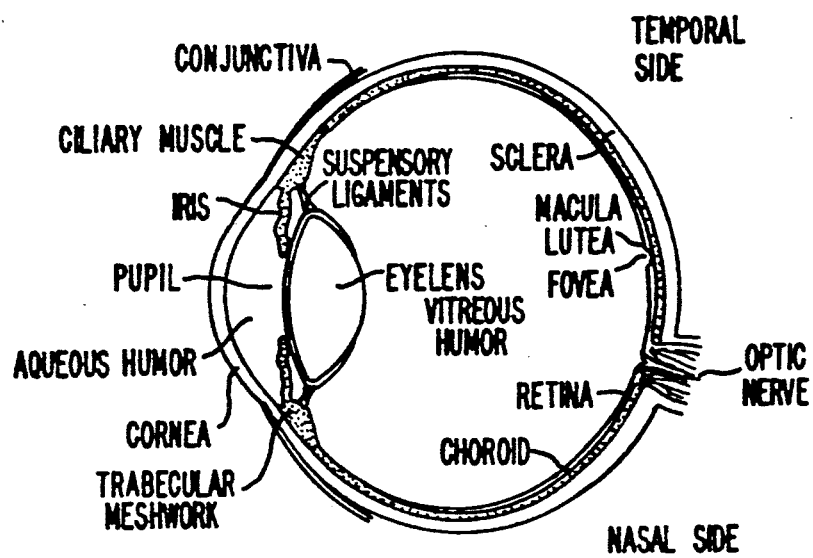
FIG._7.
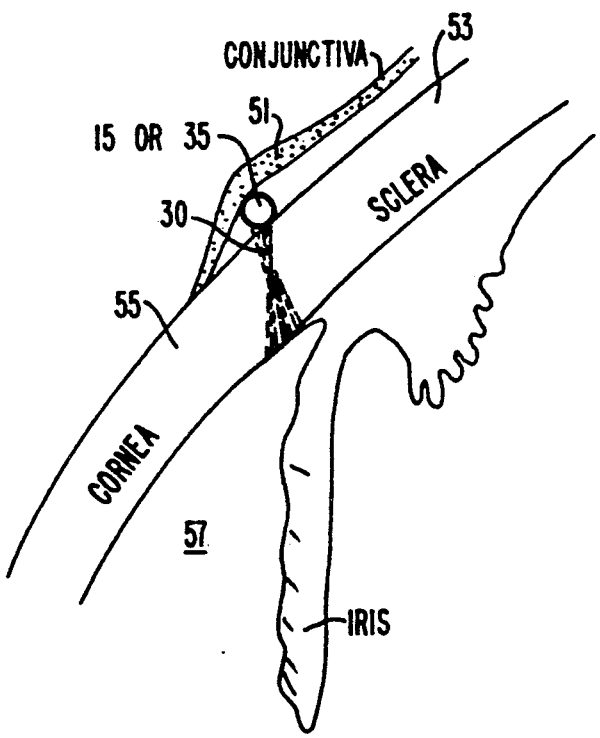
FIG._8.

LASER SCLEROSTOMY PROCEDURE

BACKGROUND OF THE INVENTION

The present invention relates generally to laser delivery probes and uses thereof, and more particularly, to a laser probe especially adapted for ophthalmologic applications and its use in treating glaucoma with a filtering procedure.

Glaucoma is a long-term condition where the fluid pressure inside the eye, the intraocular pressure, remains above normal for extended periods of time. This abnormal condition, if not treated properly, can lead to blindness. The high internal fluid pressure tends to cut off needed oxygen from the retina, which, if continued for a time, can cause retina cells to die. A healthy eye allows fluid to pass out through the trabecular meshwork adjacent the iris, and then through the schlemm canal and into the sinuses. Intraocular pressure builds up to unacceptable levels when this passage becomes blocked. Indeed, glaucoma is one of the chief causes of blindness, worldwide.

The current goal in the management of the patient with advanced glaucoma is the reduction and control of this intraocular pressure. Unfortunately, it is often difficult to achieve a desired pressure level in a particular patient by medical therapy because of the complexity of the disease. All too frequently, intraocular pressure continues to increase, or at least remains high, when the patient is being treated for the condition with a maximum level of medication. As a result, other, more invasive alternatives generally must be used.

These invasive alternatives include various surgical techniques of forming an opening into the eye in order to provide a fluid passage that relieves the high intraocular pressure in glaucoma patients. One method involves treatment of the trabecular meshwork with a light beam from an argon laser, without surgery, in an attempt to restore an outflow of fluid through this meshwork. The laser beam is directed through the cornea and against the trabecular meshwork. Current studies, however, have shown that a significant percentage of these procedures fail after some period of time. Other lasers, such as Q-switched ruby and neodymium:YAG have also been used to perform trabeculopunctures.

Another invasive method involves forming a new pathway through the sclera adjacent the cornea in order to allow aqueous fluid to pass from the anterior chamber of the eye, through the pathway and into a region under the conjunctiva. A flap is first opened in the covering conjunctiva by making straight line incisions along three sides of a rectangle, in a position alongside the cornea. The sclera is exposed by folding back this flap. A small opening is then formed in the sclera by either an incision (external filtration surgery) or a laser light beam. Carbon dioxide, neodymium:YAG in the free running mode, and excimer lasers have been used to perform sclerostomies. After the opening is formed, the conjunctival flap is sewn shut. Neither of these methods, however, have provided a complete solution. Surgical intervention of the conjunctiva can cause complications because of surgical trauma, and the necessary sewing shut of the conjunctival flap. External filtering surgery results in successful lowering of the intraocular pressure in 65% to 85% of the cases, depending on the condition of the eye.

Accordingly, it is a primary object of the present invention to provide an improved sclerostomy procedure and fiber optic probe for use in the procedure that is simpler, more effective and long lasting, and which is less damaging than current procedures.

It is another object of the present invention to provide a procedure and fiber optic probe for use in the procedure that can be performed on an outpatient basis, in an office, clinic or hospital.

SUMMARY OF THE INVENTION

These and additional objects are accomplished by the present invention, wherein, briefly and generally, according to one aspect, a round fiber optic probe is provided that directs focused light out of its side by use of a combination of a reflecting surface at the fiber end and lens action of a fiber side surface. Anti-reflection coatings for preventing escape of light from a backside of the probe are avoided. An appropriate light blocking element is used instead. In a preferred form, the probe includes a partial canula on an outside surface for added strength in addition to blocking light.

According to another aspect of the present invention, an improved sclerostomy procedure is performed with a probe, such as described above, that delivers laser light from its side. A small hole is first made in the conjunctiva layer of the eye so that the probe can be inserted through it. The probe is then gently advanced subconjunctivally and placed tangential to the limbus. This probe insertion produces minimal disturbance to the conjunctiva. The probe is then positioned with its light exiting side against the sclera in a position at the limbus adjacent the cornea, and laser light delivered by the probe forms the desired hole in the sclera. Since only a small hole, rather than a larger flap, need be formed in the conjunctiva, there is minimal scarring in the healing process and no sutures are required, or at most, one suture is placed at the conjunctiva hole. This result of performing the procedure with a side delivery fiber optic probe greatly simplifies the procedure and improves the success rate of the procedure. In addition, because of minimal scarring, it is easy to repeat the procedure.

Additional objects, advantages and features of the various aspects of the present invention will become apparent from the following description of its preferred embodiments, which description should be taken in conjunction with the accompanying drawings.

BRIEF DESCRIPTION OF THE DRAWINGS

FIG. 1 shows in general a laser delivery system in which the improved probe embodiments of the present invention may be utilized;

FIG. 2 is a cross-sectional view of a probe provided as part of the system of FIG. 1, according to a first embodiment;

FIG. 3 is a sectional view of the probe of FIG. 2, taken at section C—C thereof;

FIG. 4 is a sectional view of the probe of FIG. 2, taken at section D—D thereof;

FIG. 5 shows a fiber optic probe provided as part of the system of FIG. 1, according to a second embodiment;

FIG. 6 is a sectional view of the probe of FIG. 5, taken at section E—E;

FIG. 7 is a cross-sectional view of a human eye; and

FIG. 8 is an enlargement of a portion of the eye cross-section of FIG. 7, additionally illustrating a sclerostomy procedure according to the present invention.

DESCRIPTION OF THE PREFERRED EMBODIMENTS

Referring initially to FIG. 1, a probe assembly 11 includes a length of flexible optical fiber 13. In addition to an outer protective sheath that exists on the usual, commercially available optical fibers, an additional outer protective layer is usually desirable. At one end of this length of optical fiber is a connector 12 for attachment of the fiber to a laser. A laser 9 is schematically illustrated with an optical system 10 that focuses the laser output into the connector end of the optical fiber. At the other end of the assembly 11 is an enlarged diameter handle portion 14 and a probe 15. Optical radiation from the laser 9 travels along the optical fiber 13 and exits the probe 15 in a manner that has significant advantages for performing an ophthalmologic application described hereinafter.

Referring to FIG. 2, a cross-sectional view of the probe 15 of FIG. 1 is illustrated, in a first embodiment. This probe must be of minimal diameter in order to minimize the trauma, reach the target site more easily, and make a small hole in the sclera. The optical fiber preferably includes a round core 16 of 200 microns in diameter and a surrounding cladding 20 made of quartz material of different refractive indices. The core 17 and cladding 20 have centers of curvature at a longitudinal axis 17 of the optical fiber. A protective sheath 24 of the optical fiber is removed for a distance adjacent its end. A cylindrically shaped quartz tube 25 is opened at one end for receiving the optical fiber and forms an air tight attachment with its sheath 24. An opposite end of the sleeve 25 is enclosed, thereby forming a trapped volume 22 of air within the sleeve 25. Thus, an air interface is provided adjacent an end surface 21 of the optical fiber core 16 and cladding 20. In addition, air surrounds the exposed core/cladding end segment of the fiber, the walls of the sleeve 25 being spaced apart from the fiber cladding 20 by the sheath 24. The sleeve 25 is positioned with a longitudinal center axis that is substantially coincident with the optical fiber axis 17.

The purpose of the fiber end surface 21 is to reflect out of the probe 15 as a beam 30 as much of the optical radiation as possible that reaches the fiber end. This reflection results from the core 16 having a much different refractive index than that of the surrounding air. The surface 21 is most conveniently made to be planar, but could be given a more complex shape in order to better control the characteristics of the emerging beam 30. The surface 21 is formed at an angle $\theta$ with the fiber axis 17. This surface 21 is at an incidence angle that exceeds the critical angle for substantially all of the optical rays travelling down the fiber. The surface 21 directs the beam 30 outward with an axis 31 that is as close to being orthogonal with the fiber axis 17 as possible. It is this side delivery of the laser radiation beam 30 that allows the probe 15 to be advantageously utilized in the ophthalmologic procedure described hereinafter.

The optimum angle $\theta$ depends upon the refractive index of the core material 16, the wavelength of the optical radiation to be reflected, and the numerical aperture of the optical fiber. Generally, it will be within a range of substantially 35 to 45 degrees. For radiation within the infrared range, an index refraction of 1.47 for a typical quartz fiber core 16, and a fiber numerical aperture of 0.21, the angle $\theta$ which reflects substantially all of the radiation in the fiber is about 39°. That results in the exiting beam 30 having a center line 31 making an angle of about 79° with the optical fiber axis 21, or the angle $\phi$ of FIG. 2 being about 11°, if it is assumed that the probe is submerged in water. Since the probe is designed for carrying out a surgical procedure on human patients, this assumption is generally correct since tissue to be contacted by the outside surface of the sleeve 25 is mostly water.

With reference to FIG. 4, the operation of the probe 11 to deliver a focused beam 30 is described. Because of its air interface, the core 16 and cladding 20 of the fiber within the sleeve 25 act as a cylindrical lens to direct the radiation beam 30 to a substantial line focus 32 that extends generally in the same direction as the optical fiber axis 17. Assuming again that a radiation exiting area of the sleeve 25 is in contact with water, the sleeve/water interface has a lesser effect in shaping the beam 30. The shape is controlled primarily by the air interface of the cladding 20 in an area thereof through which the optical radiation exits after reflection from the surface 21. This one-dimensional focusing ability of the probe is an advantage in efficiently using the available laser optical radiation intensity. It also controls the size of the beam 30 in order to form a very small hole in the sclera of an eye by carrying out the ophthalmologic procedure described hereinafter. The position of the line focus 32 depends upon the refractive indices and the size of the fiber core 16 and cladding 20. For the size of the core used, 200 microns, the focus is about 0.5 mm from the outside of the sleeve 25 when commercially available quartz fibers are utilized. A focal distance of less than 1 mm is desirable for use in the ophthalmologic procedure described below.

It will be recognized that reflection of a small percentage of the exiting light beam 30 will be present at each interface of different materials through which it travels in exiting the probe. Some control of this reflected light is desirable, primarily to avoid burning tissue of the patient on the backside of the probe and for safety reasons. In the embodiment illustrated in FIGS. 2–5, a layer 28 of opaque, reflective material is coated on an outside surface area of the sleeve 25 to block the path of such reflected light. A pure gold coating is preferred. The coating 28 preferably extends over the top half of the sleeve 25, half-way around its outer circumference as shown in the cross-sectional view of FIG. 3. Its dimension along the length of the sleeve 25 is sufficient to cover all regions where reflected or scattered light is likely to emerge.

Such a coating is difficult to make on surfaces having a small radius of curvature, and often do not come out uniform. For this reason, and in order to provide additional strength to the brittle quartz materials of the probe of FIGS. 2–4, a modification is shown in FIGS. 5 and 6 where a canula 37 replaces the reflective coating 28. Elements of the embodiment of FIGS. 5 and 6 which correspond to those of the embodiment of FIGS. 2–4 are identified by the same reference number, but with a prime (') added.

The canula 37 is a separate, single piece stainless steel element added to surround the sleeve 25'. The sleeve 25' is completely surrounded by a full canula at its open end while about one-half of the circumference of the sleeve is covered by a half canula along a length where optical radiation exits from the probe. Strips of adhesive 40 hold the canula 37 tightly against an outside surface of the quartz tube 25', thereby to add a considerable amount of strength to the probe assembly.

For use in the ophthalmologic procedure to be described, the diameter of the overall probe 15 (embodiment of FIGS. 2–4) or 35 (embodiment of FIGS. 5 and 6) needs to be very small. A maximum diameter of less than 1 mm is easily accomplished with these designs. Indeed, a preferred outside diameter of the sleeves 25 and 25' is less than 0.5 mm and, as a specific example, can be 0.46 mm. The diameter of the optical fiber core 16 is selected to be within a range of 0.1 to 0.3 mm, and in a specific example being 0.2 mm.

It is this small size and side delivery of optical radiation that makes possible an improved procedure for forming a small hole in the sclera adjacent the cornea of a patient's eye. As shown in FIG. 8, the probe 15 or 35 is positioned under a patient's conjunctiva 51 in one eye. A side of the probe is positioned against the eye's sclera 53 in order to direct its radiation beam 30 through the sclera in a region immediately adjacent a cornea 55 tangential to the limbus. The goal of this procedure is to open a small passage in the sclera of 0.2 to 0.3 mm in cross-sectional size. This then provides a fluid path from the anterior chamber 57 within the eye to a region under the conjunctiva. This fluid path relieves internal eye pressure, thus providing a cure for glaucoma.

Because the probe is so small, and because the radiation beam 30 exits from its side, its positioning against the sclera 53 requires only that a hole of about 1 mm or less be made in the conjunctiva. The fiber probe is then positioned through that hole, and after the procedure is completed, the hole is usually allowed to heal itself, after the probe is removed, without the necessity of any sutures. However, one very fine suture is occasionally placed at the conjunctiva hole.

The type of laser 9 that is desired for this procedure is one generating an output beam that is within the infrared range of the optical radiation spectrum, preferably substantially within a wavelength range of from 1.8 microns to 3.2 microns. This wavelength range is highly absorbed by water, the primary component of the sclera through which a hole is being formed. High absorption of the radiation by the sclera results in efficient use of the energy and nearly complete absorption by the sclera itself without other portions of the eye under the sclera being undesirably heated. A holmium laser, having an output around 2.1 microns, is preferred. Alternatively, lithium, with an output of about 1.94 microns, or erbium, with an output of about 2.94 microns, may be utilized.

The optical radiation from the laser is preferably applied to the sclera by a series of pulses. Energy in each pulse within a range of from 50 mJoules to 350 mJoules is preferably generated in an output beam of the laser 9. An convenient pulse repetition rate can be utilized, a rate of 5 pulses per second typically being used. If the amount of energy per pulse is about 100 mJoules, a total exposure time of from 3–6 seconds duration is sufficient for the sclerostomy.

Although the various aspects of the present invention have been described with respect to their preferred embodiments, it will be understood that the invention is entitled to protection within the full scope of the appended claims.

It is claimed:

1. An ophthalmologic procedure, comprising the steps of:

forming a hole through a conjunctiva layer of a patient's eye, providing a probe at an end of a length of an optical fiber, said probe characterized by directing substantially an entire light output thereof through a side area near an extreme probe end, inserting said extreme probe end through said conjunctiva hole, positioning said probe side area against an outer surface of a sclera of the patient's eye tangentially to the limbus and adjacent a cornea, thereby to form a light path from the probe against the sclera, and exposing the sclera to at least one pulse of laser light through the probe side area sufficient to make an opening through said sclera.

2. An ophthalmologic procedure, comprising the steps of:

providing a probe at an end of a length of optical fiber, said probe including a sleeve attached to said fiber in a position surrounding and enclosing said fiber end in a manner to provide an interface with a surface formed by the fiber at a critical difinite angle with respect to a longitudinal axis of the fiber in order that substantially all of any laser light traveling therealong is reflected out of a defined area of a side surface of said fiber and through a facing defined region of a side of said sleeve, at least the defined region of said sleeve being substantially transparent and positioned a distance from said fiber side defined area in a manner to provide an air gap therebetween, said probe further being characterized by an absence of any anti-reflection coating on said first fiber end and sleeve in the path of laser light exiting from the fiber and sleeve, thereby resulting in some laser light being reflected by fiber and sleeve surfaces back toward a region of the sleeve that is opposite the defined region of said sleeve, and means carried by said probe for blocking said reflected laser light from being directed away from the probe through the opposite region of said sleeve, forming a hole through a conjunctiva layer of a patient's eye, inserting the probe through said hole, gently advancing the probe subconjunctivally and orienting the probe with the defined region of said sleeve positioned against the sclera adjacent to the cornea, thereby to establish a laser light path from the probe against the sclera while substantially no laser light path is provided to the conjuctiva layer, and exposing the sclera to at least one pulse of laser light through the probe sleeve defined region that is sufficient to make an opening through said sclera.

3. An ophthalmologic procedure, comprising the steps of:

providing a radiation delivery probe formed at an end of a length of optical fiber and including a substantially cylindrical sleeve of substantially optically transparent material that is enclosed at one end and opened at another end, an end of a length of an optical fiber core and cladding inserted into said sleeve through said opened end of the sleeve and held fixed thereto in a manner that a volume of air is trapped between an outside surface of said cladding and an inside surface of said sleeve, said fiber end terminating in a surface oriented at a critical finite angle with respect to a longitudinal axis of said fiber, thereby to reflect out of a side of the fiber through an exiting region of a side of said sleeve substantially all optical radiation traveling down said length of optical fiber toward said end, and a canula positioned against an outside surface of said sleeve and extending substantially an entire length of said sleeve while extending around only a portion of an outside circumference of said sleeve for at least a portion of the length of said sleeve in order that said sleeve radiation exiting region remains uncovered by said canula, said canula being substantially opaque to optical radiation, forming a hole through a conjunctiva layer of a patient's eye, inserting the probe through said hole, advancing the probe subconjunctivally to position said exiting sleeve region against the sclera adjacent to the cornea, thereby to form a path of optical radiation from the probe to the sclera, and exposing the sclera to at least one pulse of optical radiation from the probe that is sufficient to make an opening through said sclera.

4. The procedure according to any one of claims 1 3 2 wherein the exposing step includes directing laser light along the length of the optical fiber within a wavelength range extending substantially from 1.8 microns to 3.2 microns.

5. The procedure according to any one of claims 1 3 2 wherein the exposing step includes the use of a laser which utilizes a laser medium including a material selected from a group consisting of holmium, lithium and erbium.

6. The procedure according to any one of claims 1 3 2 wherein the step of providing a probe includes providing said probe with an external diameter that is less than one millimeter.

7. The procedure according to any one of claims 1 3 2 allowing the hole to close without the use of sutures.

* * * * *

UNITED STATES PATENT AND TRADEMARK OFFICE
CERTIFICATE OF CORRECTION

PATENT NO. : 5,129,895

DATED : JULY 14, 1992

INVENTOR(S) : ARTHUR VASSILIADIS, DAVID R. HENNINGS, H. DUNBAR HOSKINS, JR.

It is certified that error appears in the above-identified patent and that said Letters Patent is hereby corrected as shown below:

| | |
|---|---|
| Column 6, line 19, in Claim 2 | insert ---air--- between "an" and "interface" |
| Column 6, line 20, in Claim 2 | replace "difinite" with ---finite--- |

Signed and Sealed this

First Day of February, 1994

Attest:

BRUCE LEHMAN

*Attesting Officer*     *Commissioner of Patents and Trademarks*